United States Patent [19]

Marshall

[11] 4,447,449

[45] May 8, 1984

[54] METHODS OF TREATING ISCHEMIC STATES

[75] Inventor: Norman B. Marshall, Portage, Mich.

[73] Assignee: The Upjohn Company, Kalamazoo, Mich.

[21] Appl. No.: 321,367

[22] Filed: Nov. 16, 1981

[51] Int. Cl.³ .................. A61K 31/275; A61K 31/34; A61K 31/35
[52] U.S. Cl. .................................. 424/304; 424/309; 424/283
[58] Field of Search ............... 424/283, 309, 269, 313, 424/304, 389

[56] References Cited

U.S. PATENT DOCUMENTS

| | | | |
|---|---|---|---|
| 3,419,578 | 12/1968 | Fitzmaurice et al. | 549/402 |
| 3,519,652 | 7/1970 | Fitzmaurice et al. | 549/402 |
| 3,673,218 | 6/1972 | Cairns et al. | 260/345.2 |
| 3,952,104 | 4/1976 | Cairns et al. | 424/283 |
| 3,993,679 | 11/1976 | Hall et al. | 260/465 D |
| 4,046,910 | 9/1977 | Johnson | 424/278 |
| 4,055,654 | 10/1977 | Cairns et al. | 424/283 |
| 4,061,791 | 12/1977 | Hall et al. | 424/304 |
| 4,067,995 | 1/1978 | Wright et al. | 424/304 |
| 4,089,973 | 5/1978 | Hall et al. | 424/309 |
| 4,095,028 | 6/1978 | Hall et al. | 560/44 |
| 4,119,783 | 10/1978 | Hall et al. | 568/43 |
| 4,159,273 | 6/1979 | Brown et al. | 260/345.2 |
| 4,159,278 | 6/1979 | Hall et al. | 260/501.15 |

OTHER PUBLICATIONS

DeBoer et al. "Autoradiographic Method for Measuring the Ischemic Myocardium at Risk: Effects of Verapamil on Infarct Size After Experimental Coronary Artery Occlusion", *Proc. Natl. Acad. Sci*, U.S.A. vol. 77, No. 10, pp. 6119–6123, Oct. 1980, Medical Sciences.
Goth et al., "Histamine", Medical Pharmacology, chap. 15, pp. 177–188, 9th ed. C. V. Mosby Co., St. Louis, (1978).
U.S. application Ser. No. 073,398, filed Sep. 7, 1979.
U.S. application Ser. No. 073,400, filed Sep. 7, 1979.
U.S. application Ser. No. 168,827, filed Jul. 10, 1980.
Reimer, K. A. et al. Lab. Invest., vol. 40, pp. 633–644 (1979).
Jugdutt, B. I. et al., Circulation, vol. 60, pp. 1141–1150 (1979).
Jugdutt, B. I. et al., Circulation, vol. 59, pp. 734–743 (1979).
Nuki, K. et al., "The inhibition of Mast Cell Degranulation in Monkey Gingiva by Disodium Cromoglycate", *J. Periodontal, Res.* 10:282–287 (1975).
Shapiro, S. et al. "Mast Cell Population in Gingiva Affected by Chronic Destructive Periodontal Disease", *Periodontics* 40:276–278 (1969).

*Primary Examiner*—Sam Rosen
*Assistant Examiner*—John W. Rollins
*Attorney, Agent, or Firm*—Joan Thierstein

[57] ABSTRACT

The present invention relates to novel methods of use for known pharmacological anti-allergenic agents including disodiumchromoglycate (DSCG) and related compounds thereof, including generally bis chromones, benzopyrans, oxamic acids and salts or esters of each, preferably lodoxamide, its THAM salt and ethyl ester. All are subsequently included in the term biologues. The methods are for the treatment of pathological cardiovascular ischemic states in animals, particularly humans. Additionally, novel compositions including the biologues of the present invention in combination with known vasodilators and feed stuffs are also disclosed.

5 Claims, No Drawings

METHODS OF TREATING ISCHEMIC STATES

DESCRIPTION

BACKGROUND OF THE INVENTION

The present invention relates to novel methods of using known pharmacological agents in man. The invention further relates to novel compositions employing these known pharmacological agents for the treatment of various conditions or diseases in animals. Particularly, the present invention relates to the use of these known pharmacological agents in the treatment of pathological cardiovascular ischemic states (PACVIS) in animals and man.

The cardiovascular ischemic states whose treatment comprises the subject matter of the present invention are those states arising from physiological processes, particularly frankly pathological processes in which necrosis develops in smooth or striated muscles or skin.

The cardiovascular ischemic state, which leads to the development of necrosis in the cardiac muscle, includes, for eample, angina, vasospastic angina, the sudden death syndrome, and the like. The ischemia resulting from these states is well known and is readily diagnosed by an attending physician or veterinarian.

The cardiovascular ischemic states directly involving necrosis of smooth or striated muscle or skin include a wide variety of diseases and conditions. Further, certain cardiovascular ischemic states are a recognized untoward consequence of numerous other diseases and conditions.

One principle class of cardiovascular ischemic states is a consequence of the various forms or types of vasospasms. Vasospasms refers to the abnormal spasm of the blood vessels, resulting in decrease in their caliber. Ischemic in this invention refers to the condition of having local and temporary deficiency of blood, due to the contraction of a blood vessel.

Although it is known that the pharmacological agents now found to be useful in the treatment of pathological cardiovascular ischemic states were previously known for use as anti-allergenic agents, the mechanism for such previously known use is not appreciated. It is known that histamine plays a role in allergic reactions. Further this amine is a potent, easily released and functional endogenous compound in the body. For example, mast cells are the cells having granules in which histamine is highly concentrated. Histamine acts on two separate and distinct receptors, termed $H_1$ and $H_2$ receptors. Both $H_1$ and $H_2$ receptors mediate the vasodilator effects of histamine. Thus, the mast cells function in the healthy vertebrate by the release of histamine. However, the specific influences of the mast cell on ischemia is not well understood. For this reason, advantages of the present invention patentably extend methods of treating pathological cardiovascular ischemic states (PACVIS). See Goth et al., "Histamine", *Medical Pharmacology*, chap. 15, pp. 117–188, 9th ed., C. V. Mosby Co., St. Louis, (1978).

Vasospasm is a condition common in adults and typically results in a deficiency of blood to muscle or skin which is then at risk of developing necrosis. Vasospasms typically result in numerous systematic manifestations, characterized by ischemic disorders. Various types of vasospasms associated with ischemia are known. See for example, *The Merck Manual*, 13th edition, Merck, Sharp and Dohme Research Laboratories, Rahway, N.J. (1977). Among the types of vasospasms are those which produce angina pectoris attributed to myocardial ischemia. These vasospasms may progress to myocardial infarction, attributable to ischemic myocardial necrosis following an abrupt reduction in coronary flow to a segment of the myocardium. Vascular spasm may also contribute to occlusion of the abdominal aorta and its branches, such as splanchnic artery occlusion, renal artery occlusion, or occlusion at the bifurcation, and peripheral vascular disorders consequent to occlusive arterial diseases. Other notable disease states whose principle long term pathology arises from vasospasms as a constituent thereof include functional peripheral arterial disorders, such as Reynaud's phenomenon, acrocyanosis, and, rarely, erythromalalgia. For example, Reynaud's disease may be idiopathic or secondary to such conditions as occlusive arterial disease. Likewise, such pathology may result from connective tissue disorders; such as, progressive systemic sclerosis, neurogenic lesions, drug intoxication, dysproteinemias, myxedema, primary pulmonary hypertension, and trauma. Much less severe in its ultimate effect is the cardiovascular ischemic state resulting from acrocyanosis.

Other disease conditions also induce pathological cardiovascular ischemic states (PACVIS) with resulting untoward effects on the affected animal. For example, arterial embolism or thrombosis may be due to a number of causes in an animal having a history of ischemia associated with vasospasm. Further, in many peripheral vascular diseases the vasospastic disorders induce pathological cardiovascular ischemic states with resulting pathological consequences.

Other vasospastic diseases also have the effect of inducing a pathological cardiovascular ischemic state, for example, immersion foot, trench foot, herpes zoster, decubitous ulcers, and diabetic gangrene.

Finally, while many cardiovascular ischemic states have been attributed in the past to excess vasospasm, measuring the extent of ischemia is a more recent development. Consequently, limiting the extent of the ischemia has likewise been difficult. For example, it has long been known in myocardial infarction that cardiac performance after recovery depends essentially on the mass of functioning muscle surviving the acute episode. Reinfarction or extension of infarct during hospitalization is common. The use of increased inspired $O_2$ concentration is one avenue of treatment. Recent animal studies suggest that reduction of the $O_2$ requirements of myocardium and an increase in coronary perfusion or reduction of after load with vasodilators reduce the area of ischemic infarction. The primary effects may be based on the lowering of peripheral resistance. These observations need further evaluation but in selected patients, especially those with elevated pressures, it appears to be appropriate in the acute stages of infarction to use vasodilators. These include such known agents as nitroglycerin, isosorbide dinitrate, trimethafan, or nitroprusside.

Measuring the ischemic myocardium at risk of necrosis is discussed by DeBoer et al. in "Autoradiographic Method for Measuring the Ischemic Myocardium at Risk: Effects of Verapamil on Infarct size after Experimental Coronary Artery Occlusion", Proc. Natl. Acad. Sci. U.S.A., vol. 77, no. 10, pp. 6119–6123, October, 1980, Medical Sciences. Such measurement in the investigation of pharmacological agents is advantageous since myocardial infarct size appears to be a function of ischemia myocardium at risk of developing necrosis. Numerous methods have been reported for assessing the effectiveness of pharmacological agents including by indirect methods. For example, one such report indicates determination of epicardial enosis. See Kloner, R. A. et al., Circulation, vol. 58, pp. 220–226 (1978). Another indirect method is described as "Factors Influencing Infarct Size Following Experimental Coronary Artery Occlusions" by Maroko, P. R. et al., Circulation, vol. 43, pp. 67–82 (January, 1971). Direct methods include postmortem injection of dyes described by Reimer, K. A. et al. Lab. Invest., vol. 40, pp. 633–644 (1979) or angiographic contrast agents described by Jugdutt, B. I. et al., Circulation, vol. 60, pp. 1141–1150 (1979), Jugdutt, B. I. et al., Circulation, vol. 59, pp. 734–743 (1979), Hoffman, M. et al. Circulation, vol. 60, II-215A (ABSTR.) (1979).

An efficient means of assessing the inhibition of cardiovascular ischemic states by a chemical agent is described by DeBoer et al., cited above. The method of DeBoer et al. determines the ability of a chemical agent to afffect infarct size. The first objective of this study is to determine the physiological status of coronary blood flood after the coronary arterial occlusion but prior to the administration of drugs. The second objective of this study is to use autoradioagraphy to test the efficacy of delayed administration of the drug, in this case verapamil, in reducing myocardiam infarction size.

The technique of DeBoer et al. for measuring the reduction of myocardial infarct size employs the techniques described in the above noted DeBoer et al. article. Thirty minutes after left anterior decending coronary occlusion mongrel dogs are randomized into control or treatment groups. Ischemic bed size (area at risk) is determined both before treatment by the injection of 99 m Tc labeled albumin microspheres with postmortem autoradioagraphy (AR-R) and during treatment by left atrial dye injection immediately before sacrifice (AR-D). Infarct size (IS) is determined six hours after coronary arterial occlusion by triphenyl tetrazolium staining and expressed as percent of left ventrical before occlusion.

In summary, the compounds of this invention are substituted in the DeBoer et al. techniques. By measuring their inhibition of the ischemic state, it is understood that the spread of necrosis is likewise inhibited which consequently reduces the size of the infarction following a coronary occlusion.

It is by this method that the efficacy of the known compounds are evaluated for the instant invention.

The known compounds employed in the novel methods and compositions disclosed herein are previously known as anti-allergenic agents specifically including disodiumchromoglycate (DSCG) and DSCG anti-allergenic biologues. Hereinafter DSCG and DSCG anti-allergenic biologues are referred to in the invention by the term "biologues." These biologues include anti-allergenic bis chromones related to DSCG. Both DSCG and bis chromones related to DSCG are described in U.S. Pat. No. 3,419,578. Further related anti-allergenic bis chromones are those described in U.S. Pat. Nos. 3,519,652 and 3,673,218. Moreover, additional compounds of the invention biologues, including anti-allergenic uses therefore, are described in U.S. Pat. No. 4,046,910, issued Sept. 6, 1977. The description of DSCG and related anti-allergenic bis chromones which are the biologues of the present invention and their anti-allergenic compositions are incorporated here by reference from U.S. Pat. Nos. 3,419,578, 3,519,652, 3,673,218, and 4,046,910.

Another class of compounds within the biologues of the present invention are the anti-allergenic benzopyrans, particularly the compounds described in U.S. Pat. Nos. 4,159,273, 3,786,071, 3,952,104, and 4,055,654. Notable among these compounds is proxicromil (FPL 57,787), 6,7,8,9-tetrahydro-5'-hydroxy-4-oxo-10-propyl-4H-naphtho[2,3-b]pyran-2-carboxylic acid, described in Example 8 of U.S. Pat. No. 4,159,273. The description and anti-allergenic compositions of these anti-allergenic benzopyrans are incorporated here by reference from U.S. Pat. Nos. 4,159,273, 3,786,071, 4,055,654, and 3,952,104.

Yet, another class of compounds within the biologues of the present invention are the anti-allergenic oxamic acids or derivatives thereof. These compounds, together with their anti-allergenic uses and compositions, are described in U.S. Pat. Nos. 3,993,679, 4,159,278, 4,095,028, 4,089,973, 4,011,337, 4,091,011, 3,972,911, 4,067,995, 3,980,660, 4,044,148, 3,982,006, 4,061,791, 4,017,538, 4,119,783, 4,113,880, 4,128,660, 4,150,140, 3,966,965, 3,963,660, 4,038,398, 3,987,192, 3,852,324, and 3,836,541. The preparations of such compounds and their anti-allergenic compositions are incorporated by reference here from the aforementioned United States patents. The most preferred biologue in the present invention is the dioxamate N,N'-(2-chloro-5-cyano-m-phenylene)dioxamic acid (lodoxamide). Among lodoxamides preferred forms are the bis THAM, (tris(hydroxymethyl)-amino methane) salt and the diethyl ester, particularly the diethyl ester.

PRIOR ART

DSCG and its anti-allergenic biologues and anti-allergenic uses, therefore, are known in the art. See the various United States patents cited above. Additionally, see copending U.S. application Ser. No. 168,827, filed July 10, 1980, which is a continuation-in-part of Ser. No. 073,398, filed Sept. 7, 1979 and Ser. No. 073,400, filed Sept. 7, 1979, for disclosure of further utility as agents for the treatment of pathological mineral resorptive states of the DSCG and anti-allergenic biologues of this invention. Further known are numerous vasodilating agents. See Goth et al., *Medical Pharmacology*, "Coronary Vasodilators", 9th ed., pp. 408–413, The C. V. Mosby Company, St. Louis, MO (1978), for examples of such agents.

With respect to DSCG, this agent has been reported to inhibit mast cell degranulation of monkey gingiva. See Nuki, K. et al., "The Inhibition of Mast Cell Degranulation In Monkey Gingiva by Disodium Cromoglycate", J. Periodontal. Res. 10:282–287 (1975) and references cited therein. Two references of particular interest cited therein are Goldhaber, P., "Heparin Enhancement of Factors Stimulating Bone Resorption in Tissue Culture", Science 147:407–408 (1965), and Shapiro, S. et al., "Mast Cell Population in Gingiva Affected by Chronic Destructive Periodontal Disease", Periodontics 40:276–278 (1969).

SUMMARY OF THE INVENTION

The present invention particularly provides:

(1) A method of arresting or preventing a pathological cardiovascular ischemic state (PACVIS) in an animal exhibiting or susceptible to the development of said PACVIS which comprises:

systemically administering to said animal an amount of an anti-PACVIS biologue effective to treat or prevent said PACVIS;

(2) In a method of preventing or treating a pathological cardiovascular ischemic state (PACVIS) with one or more known vasodilating agents comprising coronary vasodilators such as nitroglycerin, isosorbide dinitrate, or direct vasodilators such as trimethafan or nitroprusside, the improvement which comprises:

concomitantly administering an amount of an anti-PACVIS biologue which together with said known vasodilator agent or agents is effective to prevent or arrest said PACVIS;

(3) In a unit dose of a pharmaceutical composition for preventing or treating a pathological cardiovascular ischemic state (PACVIS) with one or more known coronary or direct vasodilating agents comprising nitroglycerin, isosorbide dinitrate, trimethafan, or nitroprusside, the improvement which comprises:

an amount of anti-PACVIS biologue which together with said known vasodilating agent or agents is an effective unit dose to prevent or arrest said PACVIS;

(4) an animal feed for feeding to an animal suffering from or susceptible to the development of a pathological cardiovascular ischemic state (PACVIS) which comprises:

an anti-PACVIS biologue in a concentration such that an amount thereof which will be injested by the animal over a predetermined interval contains an amount of said anti-PACVIS biologue effective to arrest or prevent said PACVIS during said predetermined interval;

(5) A feed premix for preparing an animal feed for feeding to an animal suffering from or susceptible to the development of a pathological cardiovascular ischemic state (PACVIS) which comprises:

an anti-PACVIS biologue in a concentration such that when said animal feed premix is diluted with animal feed an amount thereof which will be injected in a predetermined interval contains an amount of said anti-PACVIS biologue effective to arrest or prevent said PACVIS during said predetermined interval.

The methods or compositions of the present invention is especially preferred to treat humans for limiting infarct size following a coronary occlusion.

The present invention relates to the treatment of animals, although mammals represent particularly preferred embodiments of the present invention. Most preferred is the treatment of humans by the instant method. The present invention thus provides a method of treating both humans and valuable domestic mammals such as bovine, equine, canine, and feline species, and chickens, turkeys, geese, ducks, and other fowl.

The present invention relates to the arrest or prophylaxis of pathological cardiovascular ischemic states or of "PACVIS". The employment of sound medical therapy requires that the anti-PACVIS agent be employed prophylactically only in cases where the animal or patient is particularly susceptible to the development of PACVIS. The conditions and circumstances which increase susceptibility are readily ascertained to the ordinarily skilled physician or veterinarian and include:

(1) Coronary vasospasm which includes angina pectoris, vasospasmic angina, myocardial infarction;

(2) Peripheral vasospasm in peripheral vascular diseases which includes Reynaud's phenomenon, mesenteric ischemia, "hepatorenal syndrome";

(3) Cerebral vasospasm;

(4) A diagnosis of any disease or condition in which a PACVIS is a potential consequence such as from arrhythmic diseases.

In the prophylactic use of these anti-PACVIS agents, the dose effective for the prevention of the PACVIS is determined by patient or animal response, as discussed hereinafter for therapeutic uses, and is, in general, somewhat less than the dose required to treat a PACVIS.

A PACVIS which is arrested or prevented in accordance with the present invention includes each of the various states or conditions described above where the long-term effects on the animal are untoward, and hence the condition or state is associated with a direct or indirect pathological process.

A PACVIS is not an uncommon condition encountered in medical or veterinary practice. Accordingly, the diagnosis of a PACVIS is readily undertaken by the ordinarily skilled physician or veterinarian.

The dose regimen for the anti-PACVIS biologue employed is selected in accordance with a variety of factors, including the type, age, weight, sex, and medical condition of the mammal, the severity of PACVIS and its duration, and the particular anti-PACVIS biologue being administered. An ordinarily skilled physician or veterinarian, subsequent to the diagnosis of a PACVIS, will readily determine and describe the effective amount of the anti-PACVIS biologue to arrest the progress of the condition. In so proceeding, the physician or veterinarian would, for example, employ relatively low dosages of the anti-PACVIS biologue, subsequently increasing dose until a maximum response was obtained. Such a response is obtained when the ischemia begins to decrease and subsequently substantially ceases, or at a minimum remains much reduced.

The anti-PACVIS bioloques are the various anti-allergenic agents known in the art as discussed above. Such substances include DSCG, other anti-allergenic bis chromones, anti-allergenic benzopyrans and preferably anti-allergenic oxamic acids or derivatives (oxamates).

Various formulations may be employed including nasal drops, oral hard filled capsules, nebulized aerosols, interdermal patches, or intravenous dosages. Routes of administration include oral, insufflation, intranasal, intrabronchial, subcutaneous and intravenous; oral and insufflation being preferred.

When DSCG is employed as the anti-PACVIS biologue the compound is most preferably administered either intranasally or by insufflation. The dosage may be 5–400 mg per patient per dose but preferably is about 20 mg. Dosages administered through the nasal route are by sterile solution of from $\frac{1}{2}$ percent to 10 percent concentration with approximately 2 percent concentration preferred. Equivalent parental or oral dosages can also be administered. When dosages significantly higher than 20 mg per patient particularly by insufflation are employed, the systemic toxicity of DSCG must be carefully evaluated and subsequent dosages determined by evaluating the benefit of the drug in relation to any such toxic manifestations.

For anti-PACVIS bis chromones routes of administration which may be employed include intranasal, insufflation, oral, interdermal or as an injectable both intramuscular and intravenous. Effective dosage equivalent to the DSCG dose above may be determined and employed as described above. Initial dosages of anti-PACVIS oxamate or benzopyran may be determined by administering minimum dosages and subsequently evaluating increasing dosages determined by the benefit of the drug in relation to toxic manifestations thereof.

The preferred oxamate, lodoxamide, described above provides a particularly efficacious result when administered rectally, intranasally, by insufflation, orally, intradermally or as an injectable. The dosage range for insufflation (aerosol), rectal, intranasal or intradermal administration is from 0.0001 mg/dose to 20 mg/dose. These routes of administration have a preferred dosage range of from 0.01 mg/dose to 10 mg/dose. Oral dosage ranges for the preferred THAM salt of lodoxamide is from 0.1 mg/dose to 100 mg/dose. The diethyl ester of lodoxamide is preferably administered by the oral route at a dosage range of from 0.5 mg/dose to 30 mg/dose. Finally, the dosage range for injectable oxamates is from 0.0001 mg/dose to 5 mg/dose, preferably 0.001 mg/dose to 1 mg/dose. When dosages of above 5 mg per patient per dose orally are employed, the systemic toxicity of the anti-PACVIS oxamate or benzopyran must be carefully evaluated and subsequent dosages determined by evaluating the benefit of the biologue in relation to any such toxic manifestations.

In order to obtain the efficacious result provided by the present invention, a route of administration permitting systemic action may be required, as indicated above. Where localized effects are exerted by absorption, topical applications may be especially preferred. Thus, in the treatment of a PACVIS secondary to myocardial infarction, liquids or gels or viscous fluids may be preferred vehicles when applied to the appropriate localized chest area.

Generally, for anti-PACVIS biologues known to be orally active the oral route of administration is preferred.

Parenteral routes of administration provide the desired activity at the appropriate equivalent dose, as described above. Thus, the present method provides intravenous injection or infusion and subcutaneous injection. Regardless of the route of administration selected, the anti-PACVIS biologue is formulated into pharmaceutically acceptable dosage forms by conventional methods known to the pharmaceutical art.

When powders, pastes or gels are required, the anti-PACVIS biologue is conveniently formulated by mixture into conventional compositions. In the case of parenteral administration, sterile solutions for injection or infusion are prepared in accordance with readily available techniques. Similar sterile solutions are used for compositions in nasal administration.

The various carboxyl containing anti-PACVIS agents are all employed in any conventional, pharmaceutically acceptable form. Thus, these agents are optionally employed as free acids, esters, or salts.

The use of the anti-PACVIS biologue is, by a further embodiment of the present invention, undertaken concomitantly with other forms of conventional therapy for a PACVIS. Such other forms of conventional therapy include, for example, the various chemical therapies described in Goth et al., cited above. When such combination therapies are employed, significant anti-PACVIS effects are often obtained with reduced effective dosages of the anti-PACVIS biologue agent employed herein.

In accordance with this further embodiment of the present invention, there are provided novel pharmaceutical compositions for anti-PACVIS therapy. These novel compositions consist of combinations of two or more active agents, one such agent being an instant anti-PACVIS biologue, and the second and further agents being the heretofore known agents having the vasodilating effect. Such previously known vasodilating agents include those known as adrenergic vasodilators, direct vasodilators, and coronary vasodilators. Adrenergic vasodilators include known medicaments such as nylidrin, isoxsuprine, and isoproterenol. Direct vasodilators include other known medicaments such as hydralazine, diazoxide, minoxidil, and sodium nitroprusside. Additionally, the anti-PACVIS biologues may be combined with $\alpha$ or $\beta$ adrenergic blocking drugs. See Goth et al. supra, pp. 89-114. The $\alpha$ adrenergic blocking drugs include, for example, prazosin and $\beta$ adrenergic blocking drugs include propranolol. Such novel compositions are advantageously used in arresting a PACVIS, often permitting a reduced dosage of the instant anti-PACVIS agent than that which would be required were it the sole therapy for arresting or preventing the PACVIS.

In these novel pharmaceutical compositions, the instant anti-PACVIS biologue is employed for each unit dosage in an amount equal to the amount of the instant anti-PACVIS biologue were it the sole therapy down to an amount not less than 50 percent thereof. The other conventional anti-PACVIS agent or agents are present therein at the known amounts employed in the treatment to accomplish vasodilation.

Moreover, the present invention further provides compositions of the instant anti-PACVIS biologues exhibiting extraordinary convenience as a result of the topical activity of these agents in the treatment of PACVIS. Employed in these novel powder, paste, cream, or gel compositions are conventional ingredients to obtain the desired constituency of each composition except for the anti-PACVIS biologue.

Such powders, pastes, creams or gels contain an effective amount of the anti-PACVIS biologue such that an application of a predetermined quantity of the powders, pastes, or gels to the localized area result in the desired anti-PACVIS effect. Such powders, pastes, or gels are formulated by conventional means as is known in the art, and particularly include the combination of an instant anti-PACVIS biologue with a conventional carrier (for example, powders: lactose, magnesium stearate, starch, talc; paste: stearic acid, glyceryl monostearate, cold cream; gel: polyoxyethylene glycol; creams: spermacet, cetyl alcohol, stearic acid.) Such powders, pastes, creams or gels are particularly useful in the topical treatment of PACVIS secondary to functional peripheral diseases as described above.

Similarly, the instant invention relates to the further liquid composition comprising the anti-PACVIS biologue in solutions adapted for nasal administration. In accordance with such novel compositions, the instant anti-PACVIS biologue is present in the conventional sterile solution at a concentration such that a predetermined volume of the administered drops or aerosol contains an amount of the anti-PACVIS biologue effective to exert the desired anti-PACVIS effect on contact with the nasal tissues.

Foregoing novel compositions are preferably provided in unit dosage or package dosage forms, where the composition consists of an amount of each pharmacological agent required for a single dose or a predetermined series of doses over some predetermined interval of time. For combination therapies such unit or package dosages, therefore, may consist of a single pharmaceutical entity, containing therewithin both agents or a paired or otherwise ordered series of such discrete entities containing these agents separately. Hence, within the ambit of the novel pharmaceutical compositions provided herein are those which would include packages containing a multiplicity of discrete pharmaceutical entities in an ordered way for the administration of these novel compositions over a predetermined period of time. For example, by a preferred embodiment of the present invention such novel compositions would include discrete pharmaceutical entities containing lesser or greater amounts of the novel anti-PACVIS biologue at the time therapy is initiated with gradually increasing or decreasing amounts of the instant anti-PACVIS biologue in discrete pharmaceutical entities intended for administration subsequently as therapy progresses.

Finally, for the anti-PACVIS biologues indicated above as orally active, there are provided in accordance with the present invention feeds and feed premixes containing amonts of the instant anti-PACVIS biologue which, when present in the animal's feed, is at a concentration effective to exert the desired anti-PACVIS effect. Such feed and feed premixes are made in accordance with readily known and available techniques particularly useful in the treatment of animals where the PACVIS compromise the animal's value. Examples of a PACVIS which compromises the value of an animal include heartworm disease in dogs and aneurysms in turkeys.

Thus, the method provided by the present invention provides for the systemic administration to an animal in an amount of an anti-PACVIS agent effective to arrest or prevent a PACVIS. The anti-PACVIS agent contemplated for use in the present invention feeds and feed premixes are those compounds known in the prior art and described in the aforementioned United States patents.

Examples of preferred anti-PACVIS bis chromones are generically represented by formula I, wherein $R_1$, $R_2$, $R_3$, $R_4$, $R_5$, and $R_6$ are hydrogen, halogen (chloro, bromo, or iodo), lower alkyl (preferably alkyl of one to four carbon atoms, inclusive), hydroxy, or lower alkoxy (preferably alkoxy of one to four carbon atoms, inclusive):

wherein X is straight or branched chain polymethylene of three to seven carbon atoms, inclusive, $-CH_2-CH=CH-CH_2-$, $-CH_2-CH_2-O-CH_2-CH_2-$, $-CH_2-CO-CH_2-$, $-CH_2-(o-Ph)-CH_2$;

wherein o-Ph is 1,2-phenylene, $-CH_2-C(CH_2OH)(CH_2Cl)-CH_2-$, $-CH_2-CH(OH)-CH_2-$, or $-CH_2-CH(OH)-CH_2-O-CH_2-CH(OH)-CH_2-$; and the salts, esters, and amides thereof.

Preferred as anti-PAVCIS bis chromones in accordance with the present invention are DSCG and the various other salt and ester forms thereof, which compounds are incorporated here by reference from U.S. Pat. No. 3,419,578.

Preferred among the anti-PACVIS oxamates are the oxanilic acid derivatives represented by formula II and the phenylene dioxamic acid derivatives represented by formula III;

wherein $R_1$ is hydrogen, a pharmacologically acceptable cation or alkyl, preferably alkyl of one to 12 carbon atoms, inclusive;

wherein one of $R_2$, $R_3$, $R_4$, $R_5$, and $R_6$ is hydrogen or cyano;

wherein a second and a third of $R_2$, $R_3$, $R_4$, $R_5$, and $R_6$ are selected from the group consisting of hydrogen, nitro, amino, halo (fluoro, chloro, bromo, or iodo), alkyl (preferably alkyl of one to four carbon atoms, inclusive), hydroxy, alkoxy (preferably alkoxy of one to four carbon atoms, inclusive), and trifluoromethyl being the same or different, and wherein the remainder of $R_2$, $R_3$, $R_4$, $R_5$, and $R_6$ are hydrogen. More particularly those compounds of formulas II and III wherein $R_1$ is ethyl or protonated trimethamine and $R_3$ is cyano and $R_6$ (II) or $R_5$ (III) is chloro, the other variables being hydrogen are preferred.

The present invention thus provides a surprising and unexpected method of use and unexpectedly convenient and efficacious compositions of matter for a class of pharmacological agents previously known to be useful for unrelated pharmaceutical and other purposes.

DESCRIPTION OF THE PREFERRED EMBODIMENTS

The advantageous effects of anti-PACVIS biologues in accordance with the present invention are demonstrated by the experimental results, reported hereinafter, which are illustrative (but not limiting) as to the operation of the novel methods described above.

EXAMPLE 1

The reduction of myocardial infarct size as measured by the effects on infarct size after experimental coronary artery occlusion of lodoxamide, N,N'-(2-chloro-5-cyano-n-phenylene)dioxamic acid, (as its bis-tris(hydroxymethyl)aminomethane salt).

Following the procedure of DeBoer, W. E. et al., Proc. Natl. Acad. Sci. U.S.A., vol. 77, no. 10, pp. (6119–6123 (October, 1980) Medical Sciences, the anti-PACVIS activity of lodoxamide is assessed. The following experiment is undertaken.

Twenty-two barbiturate anesthetized dogs are treated to receive high left anterior descending coronary artery occlusions. Ischemic bed size or area at risk of developing necrosis (AR-R) is determined before treatment by injection of 99 m Tc labeled albumin microspheres with post-mortem autoradiography. The ischemic zone appears as a cold spot image. A second area at risk is determined at the time of sacrifice (AR-D) by use of an in vivo left atrial injection of thioflavin S (a fluorescent dye which stains myocardium receiving flow yellow-green, but does not stain ischemic tissue). Infarct size (IS) is determined six hours after coronary occlusion by triphenyltetrazolium staining of 5 mm transverse slices of the left ventricle. Thirty minutes after left anterior descending coronary occlusion, animals are randomized to controls (12 dogs receiving 0.9 percent saline I.V.) or lodoxamide, N,N'-(2-chloro-5-cyano-n-phenylene)dioxamic acid, (as its bis-tris-(hydroxymethyl)aminomethane salt) therapy (10 dogs receiving 20 mg per kg per hour by continuous I.V. drip). AR-R, AR-D, and IS are expressed as percentage of the left ventricle before occlusion. Infarct size is also expressed as a percentage of the area at risk. The results are shown in the table below.

TABLE I

| | Controls | Lodoxamide THAM Salt | P |
|---|---|---|---|
| AR-R | 28.7 + 2.6 | 25.3 + 3.7 | NS |
| AR-D | 28.9 + 2.5 | 25.2 + 3.1 | NS |
| IS | 30.0 + 2.7 | 13.8 + 3.2 | .002 |
| IS/AR-R | 104.5 + 3.8 | 54.5 + 11.0 | .001 |

TABLE I-continued

| | Controls | Lodoxamide THAM Salt | P |
|---|---|---|---|
| IS/AR-D | 103.8 + 3.4 | 54.8 + 8.2 | .001 |

The results of Table I indicate the oxamate, lodoxamide induces a significant protective action on ischemic myocardium by showing a significant reduction in infarct size.

A further experiment indicates the prevention of necrosis by the oxamate, lodoxamide in a prophylactic manner in a manner similar to Example I.

Example II

Fourteen dogs are treated to receive occlusion of the proximal left circumflex coronary artery. Ischemic bed size or area at risk of developing necrosis (AR-R) is determined before treatment by injection of 99 m Tc labeled albumin microspheres with postmortem autoradiography. A second area at risk is determined at the time of sacrifice (AR-D) by use of an in vivo left atrial injection of thioflavin S (a fluorescent dye which stains myocardium receiving flow yellow-green, but does not stain ischemic tissue) in a manner similar to Example 1. The animals are randomized to controls (9 dogs) or lodoxamide therapy (8 dogs receiving 20 mg/kg/hour times two infused I.V. during the period starting 30 minutes prior to and throughout 90 minutes of complete occlusion, followed by reperfusion). Infarct size (IS) is determined 24 hours after the 90 minute occlusion-reperfusion. The results are shown below in a manner similar to that described for Example I. In other words, the following Table II shows infarct size determined as a percent of the area at risk or as a percent of the total left ventricle.

TABLE II

| | Control | Lodoxamide THAM Salt | P |
|---|---|---|---|
| AR-R | 45.3 + 2.8 | 22.8 + 2.8 | 0.001 |
| AR-D | 42.8 + 1.7 | 43.1 + 3.6 | NS |
| IS | 19.5 + 1.5 | 9.7 + 1.0 | 0.001 |

The results in Table II show the oxamide therapy occasions a decrease in infarct size.

FORMULAS

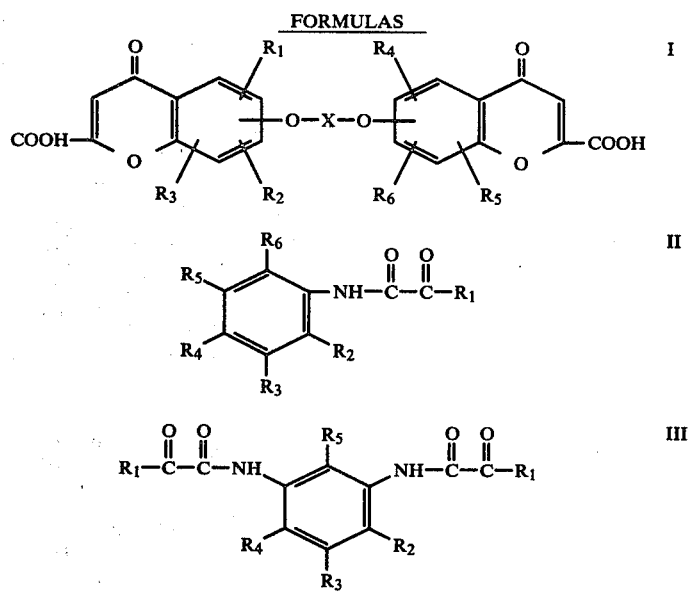

I claim:

1. A method of arresting or preventing a pathological cardiovascular ischemic state (PACVIS) in an animal exhibiting or particularly susceptible to development of said PACVIS which comprises:
   systemically administering to said animal an anti-PACVIS biologue in not less than a non-toxic amount effective to treat or prevent said PACVIS which comprises from 0.0001 mg to 400 mg per dose.

2. A method according to claim 1, wherein said PACVIS is myocardial ischemia or peripheral ischemia wherein said animal is a human.

3. A method according to claim 2 wherein said biologue is DSCG, lodoxamide, lodoxamide bis THAM salt, lodoxamide diethyl ester or proxicromil.

4. A method according to claim 3 wherein said biologue is lodoxamide bis THAM salt.

5. A method according to claim 3 wherein said biologue is lodoxamide diethyl ester.

* * * * *